United States Patent [19]

Heitz et al.

[11] 4,331,610

[45] May 25, 1982

[54] PROCESS FOR THE PREPARATION OF CARBONIC ACID ESTERS

[75] Inventors: Walter Heitz, Kirchhain; Peter Ball, Neu Otting, both of Fed. Rep. of Germany

[73] Assignee: Bayer Aktiengesellschaft, Leverkusen, Fed. Rep. of Germany

[21] Appl. No.: 112,894

[22] Filed: Jan. 17, 1980

[30] Foreign Application Priority Data

Jan. 30, 1979 [DE] Fed. Rep. of Germany ....... 2903507

[51] Int. Cl.$^3$ .............................................. C07C 68/00
[52] U.S. Cl. .................................. 260/463; 549/501; 549/473
[58] Field of Search ........................................ 260/463

[56] References Cited

U.S. PATENT DOCUMENTS 2,834,799  5/1958  Sowa .................................. 260/463

OTHER PUBLICATIONS

N. Gaylord, J. Organic Chem., 25, 1874, (1960), The Reactions of Disubstituted Carbamates with Alcohols.
P. A. S. Smith, *Open–Chain Nitrogen Compounds,* vol. 1, pp. 261, 287; (1965), Benjamin Inc. N.Y.

*Primary Examiner*—Anton H. Sutto
*Attorney, Agent, or Firm*—Gene Harsh; Lawrence S. Pope; Aron Preis

[57] ABSTRACT

The present invention relates to a process for the preparation of carbonic acid esters of mono- or polyalcohols, which is characterized in that urethanes are reacted with monoalcohols or with polyalcohols in a molar ratio of alcohol to urethane group of at least 1 to 1, in the presence of a catalyst, at reaction temperatures of between 120° C. and 270° C.

The present invention thus also relates to a process for the preparation of oligocarbonates and of polycarbonates, which is characterized in that monourethanes or bisurethanes are reacted with primary dialcohols in a molar ratio of about 1.5:1 to about 1:1.5, together with monoalcohols, in the presence of catalysts, at reaction temperatures of between 120° C. and 270° C.

7 Claims, No Drawings

PROCESS FOR THE PREPARATION OF CARBONIC ACID ESTERS

The present invention relates to a process for the preparation of carbonic acid esters of mono- or polyalcohols, which is characterised in that urethanes are reacted with monoalcohols or with polyalcohols in a molar ratio of alcohol to urethane group of at least 1 to 1, in the presence of a catalyst, at reaction temperatures of between 120° C. and 270° C.

The preparation of the urethanes is disclosed in the Zeitschrift für Naturforschung, Volume 1, 1946, pages 518 et seq. However, the further conversion of the urethanes to esters does not follow from this publication.

Monoalcohols and polyalcohols which can be used are preferably primary alcohols which can contain any desired number of C atoms. Suitable alcohols are aliphatic, cycloaliphatic, araliphatic and heterocyclic alcohols. Polyalcohols in the sense of the present invention are, for example, those with 2 to 3 alcoholic OH groups, it being possible for cyclic carbonic acid esters to form if the distance between the alcoholic OH groups in the molecule is appropriate.

The suitable monoalcohols preferably have 1 to 20 C atoms.

Examples of monoalcohols are methanol, ethanol, propanols, butanols, pentanols, hexanols, octanols, stearyl alcohol, methylolcyclohexane, benzyl alcohol, 2-phenylethanol, 2-naphthylethanol, furfuryl alcohol and the like.

Suitable polyalcohols preferably have 5 to 20 C atoms.

Examples of polyalcohols are hexane-1,6-diol, decanediols, 1,4-dimethylolcyclohexane, 1,4-dimethylolbenzene, 3(4),8(9)-bis-(hydroxymethyl)-tricyclo[5.2.1.0$^{2:6}$]decane

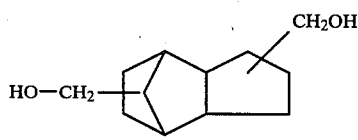

and bis-hydroxymethyl-tetrahydrofuranes and the like.

Examples of urethanes which are suitable according to the invention are monourethanes or bisurethanes, but especially those of primary alcohols.

Urethanes which are preferentially suitable according to the invention are those of the formulae Ia and Ib

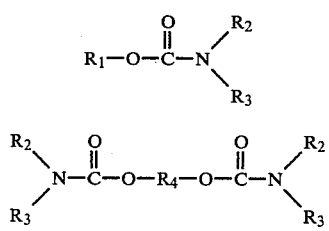

wherein
$R_1$ is a primary, optionally substituted $C_1$–$C_{18}$-alkyl, which can also contain cyclic structures and heteroatoms,
$R_2$ and $R_3$ can be identical or different and are H or $C_1$–$C_{18}$-alkyl, but preferably H, and
$R_4$ is the radical of a di-primary dialcohol with preferably 2 to 20 C atoms, which can also contain cyclic structures.

Urethanes of the formula Ia which are suitable according to the invention are, for example, isooctylurethane (isooctyl carbamate), hexylurethane, butylurethane (butyl carbamate) or (N-butyl)-isooctylurethane (isooctyl N-butylcarbamate).

Urethanes of the formula Ib which are suitable according to the invention are, for example, 1,6-hexanediol-bis-urethane, 1,10-decanediol-bis-urethane or 1,6-hexanediol-bis-(N-butyl)-urethane.

Catalysts which are suitable according to the invention are, for example, compounds of main and sub-groups 1 to 6 and of sub-groups 7 and 8 of the periodic table of the elements (see Hollemann-Wiberg, Lehrbuch der Anorganischen Chemie (Textbook of Inorganic Chemistry), edition 37–39, Verlag Walter De Gruyter and Co., Berlin 1956).

Compounds of main group 1 and sub-group 1 which are suitable according to the invention are both salt-like and covalent compounds of the metals of these groups of the periodic table, such as LiBr, butyl-lithium, LiCl, LiI, NaOCH$_3$, CuCl, AgOCO—CH$_3$ and the like.

Compounds of main group 2 and sub-group 2 which are suitable according to the invention are both salt-like and covalent compounds of the metals of these groups of the periodic table, such as MgCl$_2$, Be(O—CO—CH$_3$)$_2$, Grignard compounds, ZnCl$_2$, ZnSO$_4$, Mg(OC$_2$H$_5$)$_2$ and the like.

Compounds of main group 3 and sub-group 3 which are suitable according to the invention are in particular covalent compounds of the elements of these groups of the periodic table, such as B–(O—C$_6$H$_5$)$_3$, B(C$_6$H$_5$)$_3$, Al(OR)$_3$ (R=an aliphatic or aromatic hydrocarbon radical) and the like.

Compounds of main group 4 and sub-group 4 which are suitable according to the invention are in particular covalent compounds of the elements of these groups of the periodic table, such as orthotitanates (for example tetrabutyl orthotitanate), orthostannates (for example tetraphenyl orthostannate) and the like.

Compounds of main group 5 and sub-group 5 which are suitable according to the invention are in particular covalent compounds of the elements of these groups of the periodic table, such as amines (for example diazabicyclooctane), phosphines (for example triphenylphosphine or tri-n-octylphosphine), phosphine oxides (for example triphenylphosphine oxide), phosphonic acid esters (for example tributyl phosphite or triphenyl phosphite) and the like.

Compounds of main group 6 and sub-group 6 which are suitable according to the invention are both covalent and salt-like compounds of the elements of these groups of the periodic table, such as thioethers (for example diphenyl sulphide), thiolates (for example Na thiophenolate) and the like.

Compounds of sub-group 7 which are suitable according to the invention are both covalent and salt-like compounds of the elements of this group of the periodic table (for example manganese-II acetate).

Compounds of sub-group 8 which are suitable according to the invention are both covalent and salt-like compounds of the elements of this group of the periodic table (for example iron-III acetylacetonate).

Particularly preferred catalysts for the process according to the invention are combinations of the above-mentioned compounds and in these the electron donor and electron acceptor characteristics of the catalyst combination must be balanced relative to one another, i.e. combinations of electron donors and electron acceptors are to be employed.

Especially effective are combinations of Lewis acids and Lewis bases, especially of compounds of the main groups 1 to 3 with compounds of the main groups 4 to 6 of the periodic table of the elements.

Examples of such combinations are aluminium alcoholates in combination with amines, phosphines or phosphine oxides, lithium salts in combination with orthotitanates, or magnesium alcoholates in combination with thioethers.

The catalysts which are suitable according to the invention are employed in amounts of $10^{-3}$ to 5 mol %, based on mols of the particular urethanes employed, and these amounts apply both in the case of the use of single catalyst and in the case of the use of catalyst combinations. The molar ratio of the types of catalyst in the catalyst combinations can vary between 1:10 and 10:1.

In order to carry out the reaction according to the invention, the components, that is to say urethane, alcohol and catalyst, are warmed together, whilst stirring, to temperatures of at least 120° C. and the mixture is slowly warmed to 270° C. in the course of 5 to 10 hours and the reaction is allowed to go to completion. The batch is then separated by distillation at a lower temperature in vacuo under mild conditions and the carbonic acid ester is isolated, the yields being very good.

Since, in general, the alcohol component is employed in excess, the molar ratio of urethane group to alcohol varies between 1:1 and about 1:5 and preferably between 1:1 and 1:2.

The carbonic acid esters prepared by the process according to the invention are known compounds and, as is known, are suitable as solvents in organic chemistry and also as intermediate products or starting materials for very diverse chemical reactions.

In particular, they are suitable, in a known manner (compare German Patent Specification 1,031,512, Example 1) for the synthesis of polycarbonates by reaction with diols.

The preparation of oligocarbonates and polycarbonates can be effected in one stage by the process according to the invention, using the said urethanes, the said monoalcohols and primary dialcohols as the starting materials, suitable dialcohols being aliphatic, cycloaliphatic and araliphatic dialcohols, with the proviso that the formation of cyclic carbonates virtually does not take place under the process conditions.

The present invention thus also relates to a process for the preparation of oligocarbonates and of polycarbonates, which is characterised in that monourethanes or bisurethanes are reacted with primary dialcohols in a molar ratio of about 1.5:1 to about 1:1.5, together with monoalcohols, in the presence of catalysts, at reaction temperatures of between 120° C. and 270° C.

Preferably, the molar ratio of urethane to dialcohols for this reaction is about 1:1; the molar amount of monoalcohols, based on the molar amount of dialcohols, depends on the particular chain length which is desired, with regard to which already existing ester groups of monoalcohols (resulting, for example, from compounds of the formula Ia) must also be taken into account, and, since the monoalcohols are employed in excess, the excess can be removed by distillation. In addition, the molecular weight of the oligocarbonates or polycarbonates is controlled in a known manner by the choice of the reaction temperature and of the reaction time. Thus, oligocarbonates and polycarbonates of primary dialcohols can be prepared with diverse molecular weights in a simple manner by the process according to the invention.

With regard to the monourethanes or bisurethanes and catalysts which are suitable for the preparation, according to the invention, of oligocarbonates and polycarbonates, the definitions given initially in connection with the explanation of the preparation, according to the invention, of the carbonic acid esters again apply.

Depending on the batch and the temperature control, between 2 and 10 hours are required for the preparation, according to the invention, of the oligocarbonates and polycarbonates. The end of the reaction which is desired in the particular case can be determined, for example, viscometrically.

Preferentially suitable primary dialcohols are those with 5 to 20 C atoms; examples are those already mentioned initially in connection with the preparation, according to the invention, of carbonic acid esters, such as hexane-1,6-diol or 1,4-dimethylol-cyclohexane.

The other reaction conditions for the preparation of oligocarbonates and polycarbonates, that is to say the use of the catalysts to be employed and the amount in which they are to be employed and also the temperature control, correspond to the conditions for the preparation of the monomeric carbonic acid esters, which has already been described.

The oligocarbonates and polycarbonates obtained by the process according to the invention are known in principle and are suitable, in a known manner, for the preparation of shaped articles and films and also as coatings and additives for other plastics. The oligocarbonates and polycarbonates obtainable according to the invention are thus suitable for the known fields of application for thermoplastic polycarbonates, that is to say such as, with regard to the oligocarbonates, as secondary plasticisers for, for example, PVC and also such as for the modification of high molecular weight thermoplastic polycarbonates, for example according to U.S. Pat. No. 3,166,606.

EXAMPLE

Preparation of a carbonic acid ester 30.94 g of isooctyl carbamate, 48.90 g of isooctanol, 0.40 g of triphenylphosphine and 2.0 ml of a 20% strength solution of diisobutyl-aluminium hydride in toluene were warmed together, whilst stirring. The mixture started to boil at about 165° C. The mixture was now heated in such a way that a continuous reflux of isooctanol was set up in a Vigreux column (jacket length 30 cm) fitted on the reaction vessel. The temperature was raised continuously to 270° C. over a period of 7 hours; after that time 2.78 g (91.3% of theory) of NH$_3$ had been separated off and 24.95 g of liquid and a little solid had been distilled off (isooctanol, urethane and urea). The mixture was then subjected to fractional distillation. A fraction of 4.35 g with a boiling point$_{14}$ of 81.5 (isooctanol) and a fraction of 46.96 g with a boiling point$_{\sim 0.05}$ of 98–102 (diisooctyl carbonate) resulted. Yield 92.33%, based on urethane employed.

We claim:

1. A process for the preparation of carbonic acid esters of mono- or polyalcohols, characterized in that urethanes of the formula (Ia)

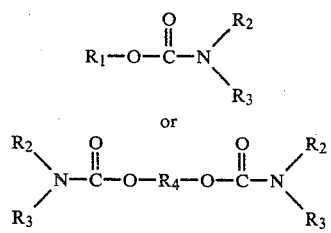

or

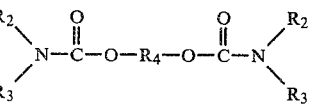

wherein $R_1$ is a primary alkyl of between 1 and 18 carbon atoms, $R_2$ and $R_3$ are hydrogen atoms and $R_4$ is a radical of a diprimary dialcohol having 2 to 20 carbon atoms are reacted with $C_1$-$C_{20}$ monoalcohols or with $C_5$-$C_{20}$ polyalcohols in a molar ratio of alcohol to urethane group of at least 1:1, in the presence of a catalyst in amounts of between $10^{-3}$ and 5 mol percent relative to the moles of said urethanes, selected from the group consisting of
  (a) saltlike or covalent compounds of main groups 4, 5 and 6 of the periodic table of elements in combination with any of
  (b) saltlike or covalent compounds of main groups 1 and 2 and subgroups 1, 2, 3, 4, 5, 6, 7 and 8 of the periodic table of elements or with any of
  (c) orthostannates, amines, phosphines, phosphine oxides, phosphonic acid esters, thioethers, thiolates, B—(O—$C_6H_5$)$_3$, B($C_6H_5$)$_3$ and AL(OR)$_3$ where R is an aliphatic or an aromatic hydrocarbon radical;
  (d) combinations of any member of (b) with any other of (b) or (c);
  (e) combinations of any member of (c) with any other of (c),
said combinations being characterized in that they are combinations of electron donors and electron acceptors by heating while stirring to at least 120° C. and by further heating to about 270° C. in the course of about 5 to 10 hours.

2. The process according to claim 1, wherein the catalyst is selected from the group consisting of compounds of the main groups 1 and 2 with any compound of the main groups 4 to 6 of the periodic table of the elements, said combinations characterized in that they are combinations of electron donors with electron acceptors.

3. The process according to claim 1, wherein the catalyst is selected from the group consisting of combinations of any of LiBr, butyl-lithium, LiCl, LiI, NaOCH$_3$, CuCl, AgOCO—CH$_3$, MgCl$_2$, Be(O—CO—CH$_3$)$_2$, ZnCl$_2$, ZnSO$_4$, Mg(OC2H5)2, B(OC6H5)3, B(C6H5)3, Al(OR)3 (R=an aliphatic or aromatic hydrocarbon radical), tetrabutyl-orthotitanate, tetraphenyl-orthostannate, diazabicyclooctane, triphenylphosphine, tri-n-octylphosphine, triphenylphosphine-oxide, tributyl-phosphite, triphenyl-phosphite, diphenyl-sulfide, Na-thiophenolate, manganese-II-acetate and iron-III-acetylacetonate, with any other thereof, said combinations characterized in that they are combinations of electron donors and electron acceptors.

4. A process for the preparation of oligocarbonates and of polycarbonates characterized in that monourethanes of formula (Ia)

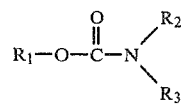

or bisurethanes of formula (Ib)

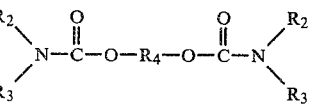

wherein $R_1$ is a primary alkyl of between 1 and 18 carbon atoms, $R_2$ and $R_3$ are hydrogen atoms and $R_4$ is a radical of a diprimary dialcohol having 2 to 20 carbon atoms are reacted with $C_5$ to $C_{20}$ primary dialcohol in a molar ratio of between 1.5:1 and about 1:1.5 and with $C_1$ to $C_{20}$ monoalcohols in the presence of a catalyst in amounts of between $10^{-3}$ and 5 mol percent relative to the moles of said urethanes, selected from the group consisting of
  (a) saltlike or covalent compounds of main groups 4, 5 and 6 of the periodic table of elements in combination with any of
  (b) saltlike or covalent compounds of main groups 1 and 2 and subgroups 1, 2, 3, 4, 5, 6, 7 and 8 of the periodic table of elements or with any of
  (c) orthostannates, amines, phosphines, phosphine oxides, phosphonic acid esters, thioethers, thiolates, B—O—$C_6H_5$)$_3$, B($C_6H_5$)$_3$ and AL(OR)$_3$ where R is an aliphatic or an aromatic hydrocarbon radical;
  (d) combinations of any member of (b) with any other of (b) or (c);
  (e) combinations of any member of (c) with any other of (c),
said combinations being characterized in that they are combinations of electron donors and electron acceptors by heating while stirring to at least 120° C. and by further heating to above 270° C.

5. The process according to claim 4, wherein the catalyst is selected from the group consisting of compounds of the main groups 1 and 2 with any compound of the main groups 4 to 6 of the periodic table of the elements, said combinations characterized in that they are combinations of electron donors with electron acceptors.

6. The process according to claim 4, wherein the catalyst is selected from the group consisting of combinations of any of LiBr, butyl-lithium, LiCl, LiI, NaOCH$_3$, CuCl, AgOCO—CH$_3$, MgCl$_2$, Be(O—CO—CH$_3$)$_2$, ZnCl$_2$, ZnSO$_4$, Mg(OC2H5)2, B(OC6H5)3, B(C6H5)3, Al(OR3 (R=an aliphatic or aromatic hydrocarbon radical), tetrabutyl-orthotitanate, tetraphenyl-orthostannate, diazabicyclooctane, triphenylphosphine, tri-n-octylphosphine, triphenylphosphine-oxide, tributyl-phosphite, triphenyl-phosphite, diphenyl-sulfide, Na-thiophenolate, manganese-II-acetate and iron-III-acetylacetonate, with any other thereof, said combinations characterized in that they are combinations of electron donors and electron acceptors.

7. The process according to claim 4 wherein said molar ratio of urethane to dialcohols is about 1:1.